United States Patent [19]

Brumfield

[11] Patent Number: 5,167,663

[45] Date of Patent: Dec. 1, 1992

[54] FEMORAL FRACTURE DEVICE

[75] Inventor: David L. Brumfield, Nesbit, Miss.

[73] Assignee: Smith & Nephew Richards Inc., Memphis, Tenn.

[21] Appl. No.: 697,155

[22] Filed: May 8, 1991

Related U.S. Application Data

[63] Continuation of Ser. No. 337,191, Apr. 12, 1989, abandoned, which is a continuation-in-part of Ser. No. 947,656, Dec. 30, 1986, Pat. No. 4,827,917.

[51] Int. Cl.$^5$ ............................................. A61F 5/04
[52] U.S. Cl. .................................................. 606/64
[58] Field of Search ............. 606/62, 64, 67; 623/16

[56]  References Cited

U.S. PATENT DOCUMENTS

| | | | |
|---|---|---|---|
| 4,281,649 | 8/1981 | Derweduwen | 128/92 YZ |
| 4,473,069 | 9/1984 | Kolmert | 128/92 YZ |
| 4,522,202 | 6/1985 | Otte et al. | 128/92 YZ |
| 4,622,959 | 11/1986 | Marcus | 606/64 |
| 4,667,664 | 5/1987 | Taylor et al. | 128/92 YZ |
| 4,733,654 | 3/1988 | Marino | 606/64 |
| 4,827,917 | 5/1989 | Brumfield | 606/64 |
| 5,041,114 | 8/1991 | Chapman et al. | 606/62 |

FOREIGN PATENT DOCUMENTS

| | | | |
|---|---|---|---|
| 118778 | 9/1984 | European Pat. Off. | 128/92 YY |
| 2406433 | 5/1979 | France . | |
| 2007980 | 5/1979 | United Kingdom . | |
| 2160775 | 1/1986 | United Kingdom | 128/1 R |

OTHER PUBLICATIONS

Huckstep, R. L.: "Huckstep Intramedullary Compression Nail" (Downs Surgical 1981).
A Grosse & Kempf interlocking femoral nail consisting of a nail and threaded locking screw.
A Russell-Taylor interlocking femoral nail consisting of a nail and a threaded locking screw.
The cover, p. 3 (title page) and p. 37 from a Grosse & Kempf brochure entitled "Locking Nail System—Indications and Clinical Cases".
Pp. 1023-1028 from the text entitled *Fractures* vol. II by Rockwood and Green.
A Russell-Taylor 1987 brochure entitled "Surgical Technique".
1983 Richards Technical Publication entitled "Richards Compression Hip Screw Technical Information".
A classic sliding hip screw consisting of a plate and a lag screw.
A Jewett nail.

*Primary Examiner*—David Isabella
*Assistant Examiner*—Debra S. Brittingham
*Attorney, Agent, or Firm*—Pravel, Gambrell, Hewitt, Kimball & Krieger

[57]  ABSTRACT

An apparatus for treating fractures of the femur including a screw and an intramedullary rod. The screw has a threaded portion and a smooth portion. The rod has a head and a stem. There is at least one opening through the head of the rod in an angled direction toward the femoral head relative to the longitudinal axis of the rod. The opening is adapted to slidingly receive the screw to permit the threaded portion of the screw, in use, to engage the femoral head and to allow sliding compression of a femoral neck or intertrochanteric fracture. An optional second opening and second screw which will also allow sliding compression may be provided to prevent rotation and to adapt the fracture device to a variety of applications.

6 Claims, 3 Drawing Sheets

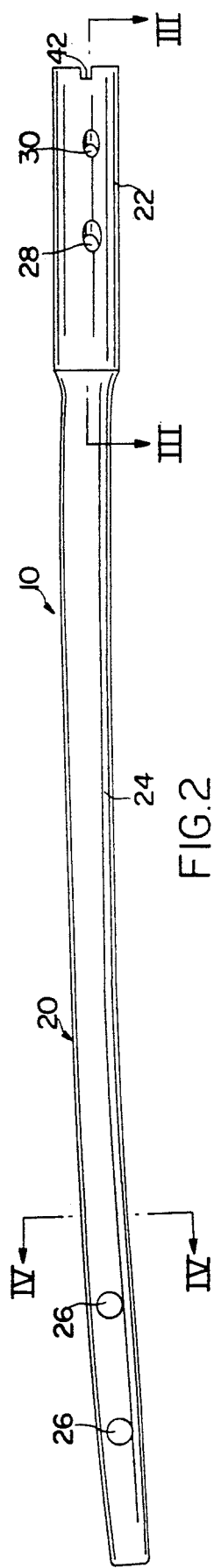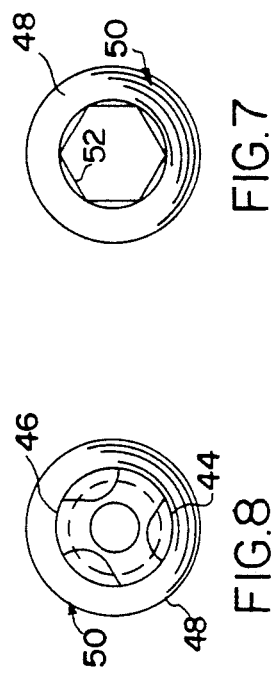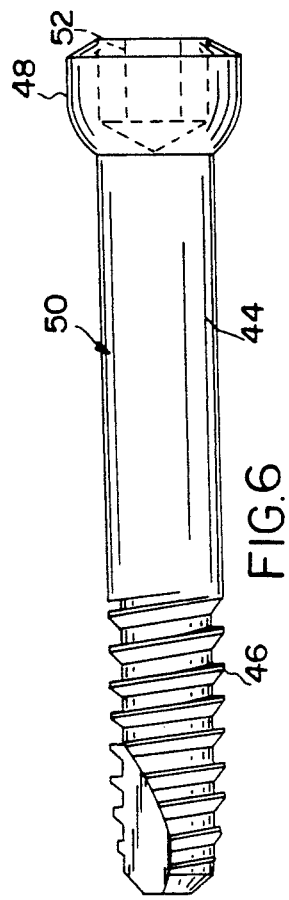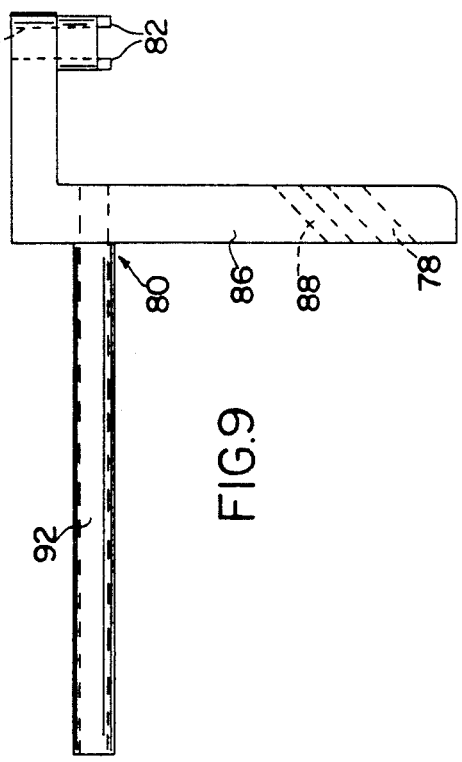

FEMORAL FRACTURE DEVICE

This is a continuation of co-pending application Ser. No. 07/337,191, filed Apr. 12, 1989, now abandoned, which is a continuation-in-part of U.S. patent application Ser. No. 06/947,656, filed on Dec. 30, 1986, now U.S. Pat. No. 4,827,917.

BACKGROUND OF THE INVENTION

1. Field of the Invention

The invention relates generally to devices for treating femoral fractures and, more particularly, to intramedullary rods.

2. Description of the Prior Art

There are a variety of devices used to treat femoral fractures. Fractures of the neck, head or intertrochanter of the femur have been successfully treated with a variety of compression screw assemblies which include generally a compression plate having a barrel member, a lag screw and a compressing screw. The compression plate is secured to the exterior of the femur and the barrel member is inserted into a predrilled hole in the direction of the femoral head. The lag screw which has a threaded end and a smooth portion is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted. The smooth portion of the lag screw must be free to slide through the barrel member to permit the adjustment of the compression screw.

Compression screw assemblies are shown by the following patents: Fixel U.S. Pat. No. 4,432,358; Callender, Jr. U.S. Pat. No. 3,374,786; Pugh et al. U.S. Pat. No. 2,702,543; Griggs U.S. Pat. No. 4,530,355; Blosser, U.S. Pat. No. 3,094,120; and Wagner U.S. Pat. No. 3,842,825. The Blosser and Wagner patents illustrate the use of multiple screws to prevent rotation of the lag screw relative to the compression plate and barrel member. A surgical bone pin which functions like a lag screw and compressing screw but which does not include a compression plate is shown by Cochran et al. U.S. Pat. No. 3,103,926.

Subtrochanteric and femoral shaft fractures have been treated with the help of intramedullary rods which are inserted into the marrow canal of the femur to immobilize the femur parts involved in fractures. A single angled cross-nail or locking screw is inserted through the femur and the proximal end of the intramedullary rod. In some varieties, one or two screws may also be inserted through the femoral shaft and through the distal end of the intramedullary rod. The standard intramedullary rods have been successfully employed in treating fractures in lower portions of the femoral shaft.

The Grosse-Kempf nail manufactured by Howmedica Company of Rutherford, N.J. is believed to be one of the earliest intramedullary nailing devices introduced into the United States. The Grosse-Kempf nail includes a threaded hole in the intramedullary rod for receiving the interlocking screw. The fully threaded screw cannot slide through the threaded hole to permit the type of compression found in the compression screw assemblies discussed above. Furthermore, the axis of the threaded hole coincides with a line between the greater to lesser trochanter and not in the direction of the femoral neck.

Zickel U.S. Pat. No. 3,433,220, which issued on Mar. 18, 1969, discloses an intramedullary rod and cross-nail assembly which is useful in treating fractures occurring in the upper one-third or subtrochanteric portion of the femur. The Zickel nail is a solid intramedullary nail having a single proximal tri-flange cross-nail which is inserted in the direction of the femoral head. The intramedullary rod is curved in two planes to mimic the shape of the femur. The solid cross section does not permit insertion over a guide rod, thus preventing the use of the Zickel nail for comminuted and distal fractures of the femur because the closed surgical technique cannot be practiced. The rigid tri-flange cross-nail is not suitable for use in treating femoral neck fractures because the cross-nail must be locked into position by a set screw to prevent backing out. Adequate compression cannot be achieved. As stated above, the sliding compression screw has been found to be most effective in treating femoral neck fractures.

The commercially available Kuntscher Y-nail includes a flanged cloverleaf shaped intramedullary nail which is inserted through a hole in a single femoral neck nail. The rod includes a longitudinal slit. The Kuntscher device is indicated only for unstable trochanteric fractures. Neither the Kuntscher device, nor the Zickel nail, includes distal anchoring means and both therefore are not useful for treating distal fractures. The femoral neck nail of the Kuntscher device, which is angled toward the femoral neck, is locked into place by the intramedullary rod. Thus, the Kuntscher Y-nail is also not indicated for femoral neck fractures.

The Russell-Taylor interlocking nail system manufactured by Richards Medical Company of Memphis, Tenn. includes an intramedullary rod having two pairs of coaxial holes through its proximal end. The axes of the pairs of holes intersect to provide a left or right orientation for insertion of a single locking screw. The screw is designed to pass from the greater to the lesser trochanter. There is not sufficient mechanical support to allow usage of the locking screw in the direction towards the femoral head because the second pair of coaxial holes weaken the nail when loaded in that direction. Further, the locking screw is a fully threaded screw which does not permit sliding of the screw relative to the intramedullary rod.

Another bone-nail which permits left-right orientation by means of "criss-cross" nail holes is shown by Ender U.S. Pat. No. 4,475,545.

For unstable subtrochanteric fractures, the extreme loads have frequently caused implants, such as hip compression screw plates, to fail. In cases of severe comminution of the femoral shaft, existing interlocking nails have at times not provided adequate strength.

It is an object of the present invention to provide a single device which can be used to treat a variety of fractures. Such a device would permit hospitals to reduce their inventories of orthopaedic surgical devices and thereby reduce costs.

It is a further object of the present invention to provide a device which combines the superior mechanical and biological attributes of intramedullary fixation with the proven benefits of the sliding compression screw for fracture reduction.

It is a further object of the present invention to provide a stronger fracture device which more closely approximates the performance of the unbroken bone.

SUMMARY OF THE INVENTION

The present invention provides an apparatus for treating fractures of the femur which marries the fixation attributes of an intramedullary nail with the proven benefits of the sliding compression screw. The apparatus of the invention provides a single device for treating a variety of femoral fractures, which heretofore have required more than one device. The apparatus comprises a screw and an intramedullary rod. The screw includes a threaded surface adapted in use to engage the head of a femur and a smooth surface adapted in use for continuous sliding compression of selected fractures.

The intramedullary rod has a longitudinal axis, a proximal head and a stem distal thereto. The longitudinal axis may curve in at least one portion of the stem to align the rod along the length of the marrow canal of the femur when the rod is inserted in the femur. The curve of the longitudinal axis, and thus the curve of the stem of the rod, is through a single plane.

The head has a first opening extending therethrough in an angled direction relative to the longitudinal axis of the rod such that when the rod is in position within the marrow canal of the femur, the axis of the opening is directed toward the head of the femur. The head may also have a second opening extending therethrough which is also in an angled direction relative to the longitudinal axis of the rod. The axes of the first and second openings are generally parallel to each other.

The apparatus may further include means, such as a nail, screw or bolt, associated with the rod for preventing rotation of the head of the femur relative to the first screw.

One embodiment of the apparatus includes a second screw adapted in use to be optionally insertable through a portion of the femur and the second openings to prevent rotation of the femoral head. The insertion of the second screw is indicated in treating femoral neck and unstable intertrochanteric fractures.

BRIEF DESCRIPTION OF THE DRAWINGS

The present invention can be better understood by reference to the drawings in which:

FIG. 2 is an elevation view of the intramedullary rod of FIG. 1 (right nail is shown);

FIG. 6 is an enlarged elevation view of the screw of the present invention;

FIG. 7 is a top end view of the screw of FIG. 6;

FIG. 8 is a bottom end view of the screw of FIG. 6;

FIG. 9 is a side elevation view of a tool used to align and drive the apparatus of the present invention;

DETAILED DESCRIPTION OF THE PREFERRED EMBODIMENTS

Figure 1:
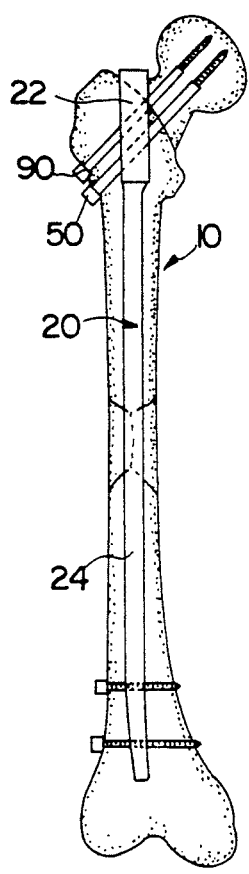
FIG. 1 is a view of the intramedullary rod of the present invention in place in a femur (several fracture patterns shown)

FIGS. 1 through 14 illustrate the preferred embodiments of the femoral fracture devices 10 and 110 of the present invention.

The femoral fracture device 10 includes intramedullary rod 20, lag screw 50, optional set screw 60 and an optional additional anchoring means 90. The device may be made of any suitable strong, biocompatible material but stainless steel, titanium or chrome-cobalt are preferred. A tool 80 used for aligning the rod 20, lag screw 50 and the optional additional anchoring means 90 is shown in FIG. 9.

Intramedullary rod 20 includes a proximal head 22, a stem 24 distal to the head 22 and a longitudinal bore 32. Referring to FIG. 2, the longitudinal axis of rod 20 curves through one plane along the stem 24 to align the rod along the length of the marrow canal of the femur.

Figure 3:
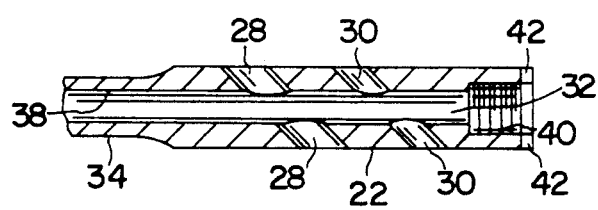
FIG. 3 is a cross section of the head of the intramedullary rod of FIG. 2 taken through the line III—III.
Figure 5:
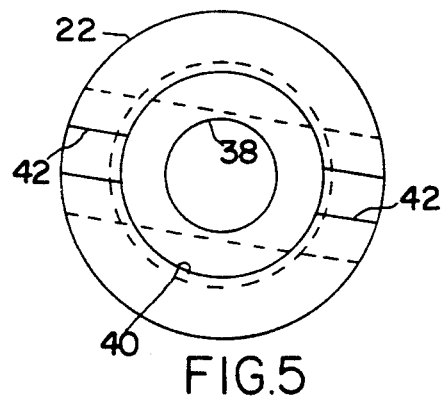
FIG. 5 is a top end view of the intramedullary rod of FIG. 2.

The head 22 includes at least two pairs of holes, a proximal pair of holes 30 and a distal pair of holes 28. Referring to FIG. 3, the holes of a pair are coaxially arranged on a common axis extending through bore 32 in an angled direction relative to the longitudinal axis of rod 20. The common axes of the distal and proximal pairs of holes 28 and 30, respectively, are generally parallel to each other. The diameter of the distal pair of holes 28 is preferably greater than the diameter of the proximal pair of holes 30. The surface of rod 20 which defines the holes 28 and 30 is smooth to permit sliding contact with lag screw 50 and optional additional anchoring means 90 for sliding compression of a femoral neck or intertrochanteric fracture. A threaded counterbore 40 with slots 42 is provided at the end of head 22 to receive the set screw 60 and prongs 82 of tool 80, respectively. The axis of slots 42 is parallel in one plane with the common axes of holes 28 and 30 to insure alignment with tool 80. Axes of both slots 42 and holes 28 and 30 may be angled (as shown in FIG. 5) with respect to the plane containing the curve of stem 24 to position screw 50 in the same anteverted direction of the normal femoral head.

Stem 24 includes at least one, and preferably two pairs of holes 26. Both holes of a pair of holes 26 are coaxially arranged on a common axis extending through the bore 32 in a transverse, preferably perpendicular, direction relative to the longitudinal axis of the rod 20. Holes 26 are adapted to receive any suitable known anchoring means (not shown), such as nails, screws or bolts to secure rod 20 within the marrow canal of the femur. Distal anchoring provided by holes 26 prevents shortening and rotation of unstable shaft-fractures.

Figure 4:
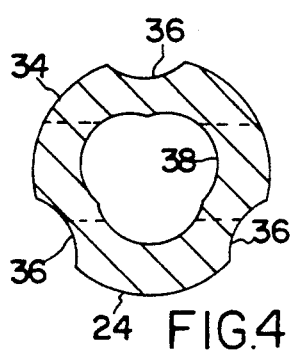
FIG. 4 is a cross section view of the stem of the intramedullay rod of FIG. 2 taken through line IV—IV.

The stem 24, as shown in FIG. 4, resembles a clover leaf in shape. The interior surface 38 of rod 20 is also clover-leaf shaped. The exterior surface 34 of stem 24 is defined by three arcs separated from each other by scalloped sections 36. The scalloped surface provides space surrounding the rod 20 for the endosteal blood supply. A sufficient flow of blood throughout the region is necessary to promote healing.

The closed cross sectional construction of rod 20 provides approximately a ten fold increase in torsional strength over the variety of prior art rods having an open cross-section formed by a slit along the length of the rod. It is known that the rods having such a longitudinal slit have experienced torsional problems. The rods can twist causing malalignment of bone segments and improper healing due to the excess shearing motion at the fracture site. The cross section of the rod 20 of the present invention is closed and is thicker than conventional rods, thereby providing a stronger construction with greater torsional stability for application in treating subtrochanteric and highly comminuted fractures.

Referring to FIG. 6, the lag screw 50 includes a smooth portion 44, a self-tapping threaded end 46 and a beveled head portion 48. A hexagonally shaped inset 52 in the head portion 48 permits insertion of a suitable tool for compression of lag screw 50. Lag screw 50 is preferably cannulated to permit insertion of a guide wire. The optional anchoring means 90 is of similar construction to permit sliding compression. Anchoring means 90 shown in FIG. 1 has a threaded portion and a smooth portion.

The set screw 60, shown in FIG. 9, has a threaded portion 62, a shaft 66 and a beveled tip 64. The set screw 60 is preferably long enough to wedgedly engage the smooth portion 44 of lag screw 50 when lag screw 50 is inserted through the distal pair of holes 28 in head 22 of rod 20. The set screw 60 secures lag screw 50 in position relative to rod 20. Counterbore 40 is preferably deeper than threaded portion 62 of set screw 60 and the shaft 66 of set screw 60 is preferably longer than that portion of bore 32 in head 22 into which the set screw is inserted prior to contacting lag screw 50 so that sufficient pressure can be applied to set screw 60 to wedge it securely against lag screw 50.

A tool 80 is shown in FIG. 9 to help align the parts of femoral fracture device 10 during application to a patient. The tool 80 includes prongs 82 to engage slots 42 of head 22 to align bore 84 with bore 32 for insertion of a (temporary) cannulated locking bolt therethrough to secure tool 80 to rod 20 for driving and for precise alignment of drilling instruments and lag screws.

By placing prongs 82 in slots 42, bores 88 and 78 of arm 86 of tool 80 align with the proximal and distal pairs of holes 30 and 28, respectively, of head 22. Lag screw 50 and the optional additional anchoring means can be inserted through the appropriate holes in rod 20 by means of tool 80. Tool 80 also includes a handle 92 for manipulating rod/tool assembly while driving into the bone marrow cavity. Handle 92 contains a keyway for attachment and alignment of a distal targeting device for aligning distal locking screws through holes 26 of rod 20.

Figure 11:
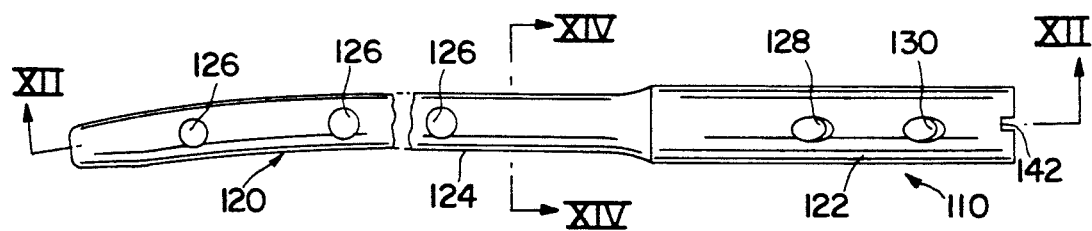
FIG. 11 is an alternative embodiment of the intramedullary rod of the present invention.
Figure 12:
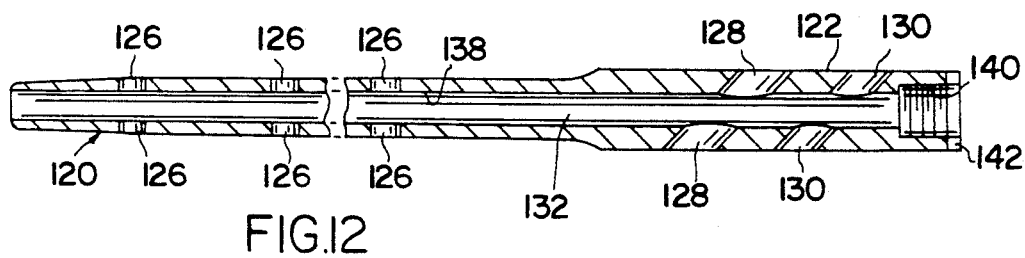
FIG. 12 is a cross section view of the intramedullary rod of FIG. 11 taken through the lines XII—XII.
Figure 14:
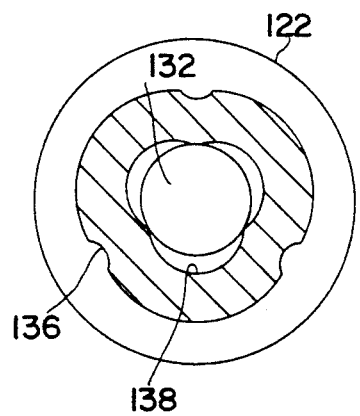
FIG. 14 is a cross section view of the stem of the intramedullary rod of FIG. 11 taken through the line XIV—XIV.
Figure 13:
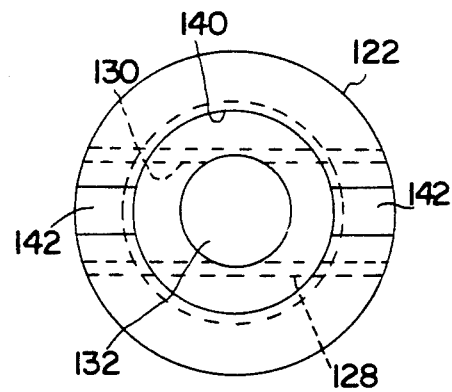
FIG. 13 is a top end view of the intramedullary rod of FIG. 11.
Figure 10:
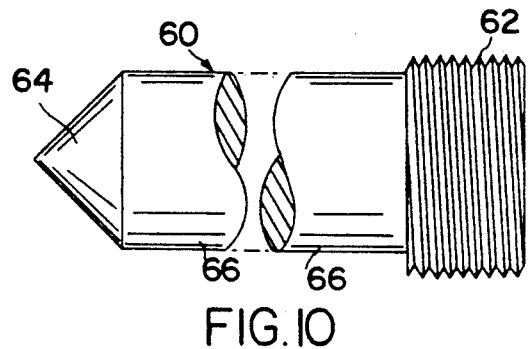
FIG. 10 is a set screw of the present invention.

An alternative embodiment of the femoral fracture device 110 is shown in FIGS. 11 and 12. Rod 120 may be of varying length for use in simple femoral neck fractures. There is no need to ream the entire length of the femoral marrow channel if there is no trauma to the region. FIG. 11 illustrates a shorter rod 120 having bore 132, a head 122 and a stem 124. Head 122 has proximal and distal pairs of holes 130 and 128, respectively, oriented in the same manner as the corresponding holes 30 and 28 in the longer version of rod 20 described above.

The shorter stem 124 of rod 120 has shown three pairs of holes 126 along its length. The holes 126 are oriented in the same manner as the corresponding holes 26 in stem 24 of rod 20. There may be any number of such paired holes to accommodate different needs. At least one pair of holes 126, however, is recommended.

Figure 1A:
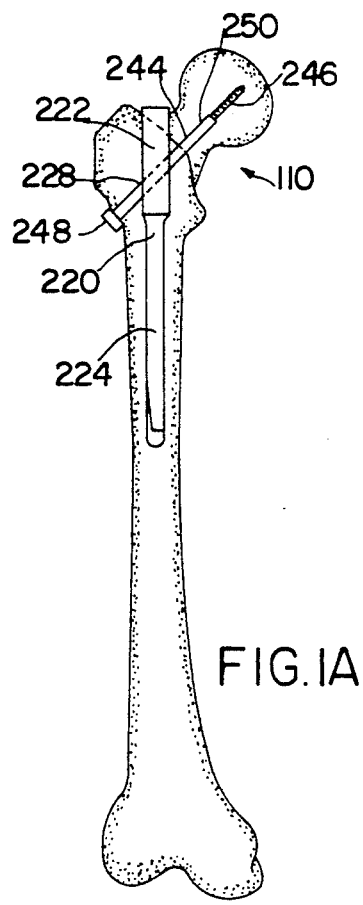
FIG. 1A is a view of an alternative embodiment of the intramedullary rod of the present invention in place in a femur.

FIG. 1A illustrates an alternative embodiment of the femoral fracture device 110. Rod 220 may be of varying length, but preferably is shorter than the rod 20 shown in FIG. 1. Rod 220 does not include an internal bore, such as bore 32. Rod 220 includes a proximal head 222 and a stem 224 distal to the head 222. The head 222 includes a first opening 228 extending through the rod 220 in an angled direction relative to the longitudinal axis of rod 220. When rod 220 is in place in the marrow canal of a femur, the axis of the opening 228 is directed toward the head of the femur. There are preferably no openings in the stem 224. A screw 250, which is similar to the screw 50 described herein, includes a threaded surface 246 at its end, a smooth surface 244 formed on the remaining major portion of its length, and a head portion 248. Screw 250 is inserted in use through opening 228 so that the threaded surface 246 engages the head of the femur. The smooth surface 244 contacts the rod 220 to permit continuous sliding compression of selected fractures.

Although only the first opening 228 is shown, a second opening, similar in position and function to the proximal head holes 30 of rod 20 in femoral fracture device 10, may be provided. In that instance, a second screw for insertion through the second opening for preventing rotation of the head of the femur relative to the first screw 250 will also be provided. The second screw includes a threaded end and a smooth surface along the remaining major portion of its length. The smooth surface permits sliding contact with the head 222 of rod 220 through the second opening.

The femoral fracture device 10, or the alternative embodiment 110, may be inserted into a patient using a known closed intramedullary surgical technique which requires minimal exposure of the femur. Image intensification equipment is employed to guide the surgeon during the procedure.

The fracture device 10, 110, may be inserted into the patient by any suitable known technique. Generally, the marrow canal of the femur is first reamed with an appropriate known reaming tool to create a void for insertion of the rod 10, 110. Progressively larger reamers are used to increase the diameter of the void. As stated above, when the shorter version 110 of the device is used, the reaming need not be very deep. The voided area within the marrow canal should be over reamed to accommodate different sized patients and to permit sufficient space for blood flow after insertion of the rod 20, 120 or 220. It is recommended that the bore be over reamed by at least one mm. A guide pin or wire may be inserted into the reamed area. Then the rod 20, 120, is guided into the reamed marrow canal of the femur. The internal bore 32 of rod 20 is necessary for driving the nail over a previously inserted guide rod which served to align the displaced fracture and guide a series of flexible cannulated reamers for preparing the narrow cavity to accept stem 24. The position of the rod 20, 120, 220 including the orientation of the holes or openings should be verified by image intensification.

When the rod is properly oriented, the tool 80 can be used to align the lag screw 50 with the distal pair of holes 28, 128 of head 22, 122. A tool may also be used to align the screw 250 with the opening 228 in rod 220. Prior to insertion of lag screw 50, 250 the area must be appropriately reamed by known techniques. A hole in the femoral head and neck is prepared to accept lag screw 50, 250 with a "step-drill" or "step-reamer" containing two diameters: a smaller diameter at its tip corresponding to the root diameter of the lag screw thread; and a larger diameter which is equal to the diameter of the smooth portion of lag screw 50, 250. This preparation allows lag screwing the femoral head and thus sliding compression of a femoral neck fracture. A guide wire is used to determine proper position of lag screw 50, 250 in the femoral head. Lag screw 50 is inserted through a sleeve which fits snugly into bore 78 of tool 80 and into holes 28, 128. The threaded end 46, 246 engages the femoral head. The smooth portion 44, 244 slides through holes 28, 128, 228. A hexagonal screwdriver or any suitable tool can be used to compress lag screw 50, 250 to a desired degree.

If there is a femoral neck fracture the compression of lag screw 50, 250 functions like a compression screw assembly to reduce the fracture. Anchoring means 90 or the second screw is then optionally inserted through a sleeve which fits snugly into bore 88 of tool 80 into the proximal pair of holes 30, 130 in head 22, 122 or into the second opening of head portion 222. The insertion of the optional anchoring means 90 or second screw is indicated in femoral neck fractures and unstable intertrochanteric fractures to prevent rotation of the femoral head and to provide auxiliary support to proximal bone fragments. The area is reamed in an appropriate manner prior to insertion of the optional anchoring means 90 or the second screw.

If the optional anchoring 90 means is not needed, for example in a subtrochanteric fracture, then the optional set screw 60 is inserted into that portion of bore 32, 132 in head 22, 122 of rod 20, 120 until the beveled tip 64 wedges against the smooth portion 44 of lag screw 50 to jam the lag screw 50 against holes 28, 128 to secure lag screw 50 relative to rod 20, 120. The threaded portion 62 of set screw 60 is tightened into the threaded portion of counterbore 40, 140 until the lag screw 50 is secure.

Image intensification equipment is used to locate and determine the orientation of holes 26, 126 for insertion of suitable known anchoring means, such as nails, screws or bolts. The insertion of the distal anchoring means in the stem of rod 20, 120 is indicated in unstable shaft fractures.

Removal of the rod 20, 120, 220 is less traumatic than removal of some varieties of known intramedullary nailing devices because the rod 20, 120, 220 is curved in only one plane. Although the femur is naturally curved in more than one plane, the removal of a rod which mimics the curves of the natural femur can cause trauma to the femur and, on occasion, can break the bone.

The femoral fracture devices 10, 110 of the present invention are biomechanically a superior method of treating a wide range of femoral fracture patterns, such as a wide range of femoral fracture patterns, such as combination neck/shaft fractures, any type of femoral neck fracture, certain intertrochanteric fractures, subtrochanteric fractures, severely comminuted shaft fractures, reconstruction of the femoral shaft, allograft reconstruction of the femoral shaft after tumor resection, and leg lengthening. Other uses will be recognized by those skilled in the art.

What is claimed is:

1. Apparatus for treating fractures of the femur comprising:
   a) a hollowed intramedullary rod having a longitudinal axis and a rod sidewall that surrounds a longitudinal bore, said rod having a proximal head and a stem distal thereto, and wherein the stem and a substantial portion of the head are adapted in use for insertion into the marrow canal of a femur;
   b) the rod sidewall having a first, generally uniform smaller wall thickness defining the stem, and a second, larger wall thickness defining the head;
   c) said head having a first smooth opening extending therethrough in an angled direction relative to the longitudinal axis of said rod such that when said rod is in position within the marrow canal of the femur, the opening is positioned to intersect the longitudinal axis of the rod, and the axis of said opening is directed toward the head of the femur;
   d) a first screw for insertion through said first opening in said head and including first and second end portions;
   e) said first screw having a threaded surface formed at the first end adapted in use to engage bone tissue of the head of the femur, and
   f) wherein said threaded section is spaced from the first opening during use for maintaining continuous sliding contact between said head of said rod and the first screw, to permit sliding compression of the selected fracture.

2. Apparatus as recited in claim 1 which further comprises:
   means associated with said rod for preventing rotation of the head of the femur relative to said first screw.

3. Apparatus as recited in claim 2 wherein:
   said head has a second opening extending therethrough in an angled direction relative to the longitudinal axis of said rod, the axis of said second opening being generally parallel with the axis of said first opening; and
   said means for preventing rotation comprises a second screw for insertion through said second opening in said head, said second screw having a threaded end and a smooth surface along the remaining major portion of its length, said smooth surface being adapted in use for sliding contact with said head of said rod through said second opening.

4. The apparatus of claim 3 wherein the second opening has a greater diameter than the first opening.

5. The apparatus of claim 3 wherein the first and second openings have smooth surfaces that engage corresponding smooth surfaces of the first screw and the rotation preventing means respectively.

6. The apparatus of claim 1 wherein the first screw has a self-tapping threaded end portion.

* * * * *